(12) United States Patent
Bacus

(10) Patent No.: US 9,625,446 B2
(45) Date of Patent: *Apr. 18, 2017

(54) METHOD AND QUANTIFICATION ASSAY FOR DETERMINING C-KIT/SCF/PAKT STATUS

(75) Inventor: Sarah S. Bacus, Hinsdale, IL (US)

(73) Assignee: Ventana Medical Systems, Inc., Tucson, AZ (US)

( * ) Notice: Subject to any disclaimer, the term of this patent is extended or adjusted under 35 U.S.C. 154(b) by 470 days.

This patent is subject to a terminal disclaimer.

(21) Appl. No.: 11/948,197

(22) Filed: Nov. 30, 2007

(65) Prior Publication Data

US 2008/0182276 A1    Jul. 31, 2008

Related U.S. Application Data

(63) Continuation of application No. 10/225,826, filed on Aug. 21, 2002, now Pat. No. 7,419,777.

(60) Provisional application No. 60/314,188, filed on Aug. 21, 2001.

(51) Int. Cl.
| | | |
|---|---|---|
| *G01N 33/567* | (2006.01) | |
| *G01N 33/574* | (2006.01) | |
| *C12Q 1/00* | (2006.01) | |
| *G01N 33/50* | (2006.01) | |

(52) U.S. Cl.
CPC ... *G01N 33/5011* (2013.01); *G01N 33/57484* (2013.01); *G01N 2800/52* (2013.01)

(58) Field of Classification Search
None
See application file for complete search history.

(56) References Cited

U.S. PATENT DOCUMENTS

| | | |
|---|---|---|
| 5,288,477 A | 2/1994 | Bacus |
| 5,536,642 A | 7/1996 | Barberá-Guillem et al. |
| 6,406,669 B1 | 6/2002 | Duan et al. |
| 2001/0044124 A1 | 11/2001 | Bacus |
| 2001/0049114 A1 | 12/2001 | Bacus |

FOREIGN PATENT DOCUMENTS

| | | | |
|---|---|---|---|
| JP | 2000-515964 | | 11/2000 |
| WO | 96/17873 | | 6/1996 |
| WO | 98/00713 | | 1/1998 |
| WO | 99/41613 | | 8/1999 |
| WO | 99/53953 | | 10/1999 |
| WO | 01/25473 | | 4/2001 |
| WO | WO01/45689 | * | 6/2001 |
| WO | 01/51924 | | 7/2001 |
| WO | 01/51928 | | 7/2001 |

OTHER PUBLICATIONS

Hines. et al (Cell Growth and Differentiation, 1995, vol. 6, pp. 769-779).*

(Continued)

*Primary Examiner* — Karen Canella
(74) *Attorney, Agent, or Firm* — Ventana Medical Systems, Inc.

(57) ABSTRACT

This invention provides methods for determining or predicting response to cancer therapy in an individual using differential image analysis of immunohistochemically stained tumor samples.

8 Claims, 12 Drawing Sheets

Immunohistochemistry for C-KIT and it's ligand, SCGF, on sample 12669b9

SCGF

(56) References Cited

OTHER PUBLICATIONS

Abstract of Hassan et al, Acta Haematologica, 1996, vol. 95, pp. 257-262.*
Arceci et al (Hematology, 2002, pp. 297-314).*
Heinrich et al (Journal of clinical Oncology, Mar. 15, 2002, vol. 20, pp. 1692-1703).*
Tsuura et al (Journal of Cancer Research and clinical Oncology, 2002, vol. 128, pp. 239-246).*
Lasota et al (ARch Pathol Lab Med, 2000, vol. 124, pp. 894-897).*
Kerr and Thorpe (Immunochemistry LabFax, 1994, p. xi).*
Joensuu et al (New England Journal of Medicine, Apr. 5, 2001, vol. 344, pp. 1052-1056).*
The abstract of Talpaz et al (Blood, Nov. 16, 2000, vol. 96, No. 11, Part 1, p. 735a).*
Page et al, Int J Oncol, published on the web, Jul. 2000, vol. 17, pp. 23-28).*
Bokemeyer et al, Journal of Cancer Research and Clinical Oncology, 1996, vol. 122, pp. 301-306).*
Druker et al., Original Articles: Efficacy and Safety of a Specific Inhibitor of the BCR-ABL Tyrosine Kinase in Chronic Myeloid Leukemia, N. Engl. J. Med. 344:1031-1037, Apr. 2001.
Heinrich et al., Hematopoiesis: Inhibition of c-kit receptor tyrosine kinase activity by STI 571, a selective tyrosine kinase inhibitor, Blood 96:925-932, 2000.
Landuzzi et al., Regular Articles: The Metastatic Ability of Ewing's Sarcoma Cells is Modulated by Stem Cell Factor and by Its Receptor c-kit, American Journal of Pathology 157:2123-2131, 2000.
Maki, ASCO 2001: Critical Commentaries Part 1: Sarcoma, Oncologist 6:333-337, Aug. 2001.
Mellinghoff and Sawyers, PPO Updates 14:1-11, 2000.
Schlom, Monoclonal Antibodies: They're More and Less Than You Think, In: Molecular Foundations of Oncology, S. Broader, Ed pp. 95-134, 1991.
Arteaga et al., "p185c-erbβ-2 Signaling Enhances Cisplatin-induced Cytotoxicity in Human Breast Carcinoma Cells: Association between an Oncogenic Receptor Tyrosine Kinase and Drug-Induced DNA Repair," Cancer Res., 54:3758-3765, 1994.
Bacus et al., "AKT2 is frequently upregulated in HER-2/neu-positive breast cancers and may contribute to tumor aggressiveness by enhancing cell survival," Oncogene 21(22):3532-3540, May 16, 2002.
Bacus et al., "Potential Use of Image Analysis for the Evaluation of Cellular Predicting Factors for Therapeutic Response in Breast Cancers," Anal. Quant. Cytol. Histol., 19:316-328, 1997.
Baselga et al., Proceedings of AACR NCI EORTC International Conference, Abstract 98, 1999.
Beck et al., "Expression of stem cell factor and its receptor by human neuroblastoma cells and tumors," Blood 86(8):3132-3138, Oct. 15, 1995.
Brognard et al., Akt/Protein Kinase B is Constitutively Active in Non-Small Cell Lung Cancer Cells and Promotes Cellular Survival and Resistance to Chemotherapy and Radiation, Cancer Res., May 2001; 61:3986-3997.
Cantley and Neel, "New insights into tumor suppression: PTEN suppresses tumor formation by restraining the phosphoinositude 3-kinase/AKT pathway," Proc. Natl. Acad. Sci. U.S.A., 96:4240-45, 1999.
Chui et al., "Immunohistochemical expression of the c-kit proto-oncogene product in human malignant and non-malignant breast tissues," British J. of Cancer, 73:1233-1236, 1996.
Ciocca et al., "Molecular markers for predicting response to tamoxifen in breast cancer," Endocrine 13(1):1-10, Aug. 2000.
Cobleigh et al., "Mutinational Study of the Efficacy and Safety of Humanized Anti-HER2 Monoclonal Antibody in Women Who Have HER2-Overexpressing Metastatic Breast Cancer That Has Progressed After Chemotherapy for Metastatic Disease," J. Clin. Oncol., 17:2639-2648, 1999.

Datta et al., "Cellular survival: a play in three Akts," Genes and Dev., 13:2905-27, 1999.
Dematteo, "The GIST of targeted cancer therapy: a tumor (gastrointestinal stromal tumor), a mutated gene (c-kit), and a molecular inhibitor (STI571)," Ann. Surg. Oncol. 9(9):831-839, Nov. 2002.
Demetri et al., "Efficacy and safety of imatinib mesylate in advanced gastrointestinal stromal tumors," New England Journal of Medicine 347(7):472-480; Aug. 15, 2002.
Dengler et al., "Urinary excretion of proteolyzed alphal-antitrypsin: specificity, quantitation, and relation to therapy response in patients with acute myeloid leukemia," Clinical Cancer Research: An Official Journal of the American Association for Cancer Research 1(2):199-205, 1995.
Digiovanna, "Clinical Significance of HER-2/neu Overexpression: Part I," PPO Updates: Princ. Practice Oncol., 13:1-9, 1999.
Glaspy, "Clinical applications of stem cell factor," Curr. Opin. Hematol. 3(3):223-229, May 1996.
Hancock et al., "A Monoclonal Antiboby against the c-erbβ-2 Protein Enhances the Cytotoxicity of cis-Diamminedichloroplatinum against Human Breast and Ovarian Tumor Cell Lines," Cancer Res., 51:4575-4580, 1991.
Hassan et al., "Stem cell factor as a survival and growth factor in human normal and malignant hematopoiesis," Acta Haematol. 95(3-4):257-262, 1996.
Hines et al., "Coexpression of c-kit and stem cell factor in breast cancer results in enhanced sensitivity to members of the EGF family of growth factors," Breast Cancer Research and Treatment 58(1):1-10, 1999.
Hines, et al., "Coexpression of the c-kit and Stem Cell Factor Genes in Breast Carcinomas," Cell Growth & Differentiation, 6:769-779, 1995.
Hortobagyi, "High-Dose Chemotherapy for Primary Breast Cancer: Facts Versus Anecdotes," J. Clin. Oncol., 17:25-29, 1999.
Joensuu et al., "Effect of the tyrosine kinase inhibitor STI571 in a patient with a metastatic gastrointestinal stromal tumor," New England Journal of Medicine 344(14):1052-1056; Apr. 5, 2001.
Johnstone et al., "Ifosfamide metabolism and DNA damage in tumor and peripheral blood lymphocytes of breast cancer Patients," Cancer Chemotherapy and Pharmacology 46(6):433-441, 2000.
Kausch et al., "Effects of troglitazone on cellular differentiation, insulin signaling, and glucose metabolism in cultured human skeletal muscle cells," Biochem Biophys Res. Commun. 280(3):664-674, Jan. 26, 2001.
Krystal et al., "The selective tyrosine kinase inhibitor STI571 inhibits small cell lung cancer growth," Clin. Cancer Res. 6:3319-3326, Aug. 2000.
Kuerbitz et al., "Wild-type p53 is a cell cycle checkpoint determinant following irradiation," Proc. Natl. Acad. Sci. USA, 89:7491-95, 1992.
Kwok and Sutherland, "Enhancement of Sensitivity of Human Squamous Carcinoma Cells to Radiation by Epidermal Growth Factor," J. Natl. Cancer Inst., 81:1020-24, 1989.
Kwok and Sutherland, "Epidermal Growth Factor Reduces Resistance to Doxorubicin," Int. J. Cancer, 49:73-76, 1991.
Lane, "p53, guardian of the genome," Nature, 358:15-16, 1992.
Li et al., "PTEN, a Putative Protein Tyrosine Phosphatase Gene Mutated in Human Brain, Breast, and Prostate Cancer," Science 275:1943-47, 1997.
Liaw et al., "Germline mutations of the PTEN gene in Cowden disease, an inherited breast and thyroid cancer syndrome," Nat. Genet., 16:64-67, 1997.
Liu et al., "Regulation of p21WAF1/CIP1 Expression through Mitogen-activated Protein Kinase Signaling Pathway," Cancer Res., 56:31-35, 1996.
Luo et al., "Cell-cycle inhibition by independent CDK and PCNA binding domains in p21Cip1," Nature, 375:159-61, 1995.
Mendelsohn, "The epidermal growth factor receptor as a target for therapy with antireceptor monoclonal antibodies," Semin. Cancer Biol., 1:339-44, 1990.
Natali et al., "Breast cancer is associated with loss of the c-kit oncogene product," Int. J. Cancer, 52:713-717, 1992.

(56) References Cited

OTHER PUBLICATIONS

Nelen et al., "Germline mutations in the PTEN/MMAC1 gene in patients with Cowden disease," Hum. Mol. Genet., 6:1383-87, 1997.

Nio et al., "Immunohistochemical expression of receptor-tyrosine kinase c-kit protein in invasive ductal carcinoma of the pancreas," Anticancer Drugs 14(4):313-319, Apr. 2003.

Pertussini et al., "investigating the platelet-sparing mechanism of paclitaxel/carboplatin combination therapy," Blood 97(3):638-644, Feb. 1, 2001.

Pietras et al., "Antibody to HER-2/neu receptor blocks DNA repair after cisplatin in human breast and ovarian cancer cells," Oncogene, 9:1829-38, 1994.

Radosevic et al., "Cell cycle regulatory protein expression in fresh acute myeloid leukemia cells and after drug exposure," Leukemia 15(4):559-566, Apr. 2001.

Remvikos et al., "Cell cycle modifications of breast cancers during neoadjuvant chemotherapy: A flow cytometry study on fine needle aspirates," European Journal of Cancer 29A(13):1843-1848, 1993.

Rusnak et al., "The effects of the novel, reversible epidermal growth factor receptor/ErbB-2 tyrosine kinase inhibitor, GW2016, on the growth of human normal and tumor-derived cell lines in vitro and in vivo," Mol. Cancer Ther. 1:85-94, Dec. 2001.

Shak, "Overview of the Trastuzumab (Herceptin) Anti-HER2 Monoclonal Antibody Clinical Program in HER2—Overexpressing Metastatic Breast Cancer," Semin. Oncol., 26:71-77, 1999.

Sliwkowski et al., "Nonclinical Studies Addressing the Mechanism of Action of Trastuzumab (Herceptin)," Semin. Oncol., 26:60-70, 1999.

Stal et al., "Akt kinases in breast cancer and the results of adjuvant therapy," Breast Cancer Res. 5:R37-R44, 2003.

Vincent et al., "Anticancer efficacy of the irreversible EGFr tyrosine kinase inhibitor PD 0169414 against human tumor xenografts," Cancer Chemother. Pharmacol., 45:231-38, 2000.

West et al., "Activation of the PI3K/Akt pathway and chemotherapeutic resistance," Drug Resist Updat. 5(6):234-248, Dec. 2002.

Winter-Vann Am et al., "Targeting Ras signaling through inhibition of carboxyl methylation: an unexpected property of methotrexate," Proc. Natl. Acad. Sci. USA 100(11):6529-6534, May 27, 2003.

Yarden et al., "Human proto-oncogene c-kit: a new cell surface receptor tyrosine kinase for an unidentified ligand," EMBO J. 6:3341-3351, 1987.

\* cited by examiner pAKT920

C-kit 747  Breast Cancer

SCF 848   Breast Cancer

C-kit 920   Bladder Cancer

SCF 920   Bladder Cancer c-Kit activity in breast cancer cells treated with SCF ligand and/or STI inhibitor.
c-Kit was immunoprecipitated from MDA-MB-361 cell lysates (50 μg total protein),
western blotted and screened with anti-phosphotryosine antibodies to detect
active c-Kit receptor. As expected, the c-Kit receptor was activated by SCF treatment,
but inhibited with as little as 1 μM STI.

NeoMarkers
CD117/c-Kit
Ab-6

DAKO
CD117/c-Kit
A4502

145kDa

Western Blot of c-Kit in HeLa cells. Rabbit polyclonal antibodies against human c-Kit from NeoMarkers (1:200 dilution) and DAKO (1:400 dilution), detected with HPR-conjugated antibodies against rabbit IgG (Amersham) and chemiluminescent substrate (NEN).

METHOD AND QUANTIFICATION ASSAY FOR DETERMINING C-KIT/SCF/PAKT STATUS

This application is a continuation of U.S. application Ser. No. 10/225,826, filed Aug. 21, 2002 which claims priority to U.S. provisional application Ser. No. 60/314,188, filed Aug. 21, 2001.

BACKGROUND OF THE INVENTION

1. Field of the Invention

This invention relates to methods for determining or predicting response to cancer therapy in an individual. The invention also relates to methods for using image analysis of immunohistochemically-stained tissue biopsies to quantify c-kit/SCF/pAKT expression and activation, and to identify efficacious anticancer compounds.

2. Background of the Invention

A primary goal of cancer therapy is to selectively kill or inhibit uncontrolled growth of malignant cells while not adversely affecting normal cells. Traditional chemotherapeutic drugs are highly cytotoxic agents that preferably have greater affinity for malignant cells than for normal cells, or at least preferentially affect malignant cells based on their high rate of cell growth and metabolic activity. However, these agents often harm normal cells.

Generally, anticancer drugs, monoclonal antibodies, chemotherapeutic or chemopreventive agents are used to produce growth arrest, terminal differentiation and cell death of the cancerous or precancerous cells (Mendelsohn, 1990, *Semin. Cancer Biol.* 1:339-44; Hancock et al., 1991, *Cancer Res.* 51:4575-80; Arteaga et al., 1994, *Cancer Res.*, 54:3758-65; Pietras et al., 1994, *Oncogene* 9:1829-38; Bacus et al., 1997, *Anal. Quant. Cytol. Histol.* 19:316-28; Bacus et al., 1999, *Breast J*; Baselga et al., 1999, Proceedings of AACR NCI EORTC International Conference, Abstract 98; Cobleigh et al., 1999, *J. Clin. Oncol.* 17:2639-48; DiGiovanna, 1999, *PPO Updates: Princ. Practice Oncol.* 13:1-9; Hortobagyi, 1999, *J. Clin. Oncol.* 17:25-29; Shak, 1999, *Semin. Oncol.* 26:71-77; Sliwkowski et al., 1999, *Semin. Oncol.* 26:60-70; Vincent et al., 2000, *Cancer Chemother. Pharmacol.* 45: 231-38). Drug-induced growth arrest or cell death is often characterized by morphological and biochemical changes associated with programmed cell death or terminal differentiation (as opposed to mitotic cell death).

Although chemotherapeutic drugs can be administered at doses high enough to bring about cell death, such doses typically produce deleterious effects on normal as well as tumor cells. Differentiating agents, and the use of lower doses of chemotherapeutic drugs and agents frequently results in growth arrest rather than cell death. Such growth arrest can be followed by apoptosis and cell death, or continued proliferation once the chemotherapeutic drugs are withdrawn. Administration of cytotoxic and chemotherapeutic drugs or ionizing radiation may also induce transient growth arrest, a state that depends largely on the function of p53 and p53-regulated cyclin-dependent kinase inhibitors (such as p16, p27, and p19) or growth inhibitors (such as TGF-β, IL-4, and IL-6). Upon removal of the chemotherapeutic drug, cells subjected to the drug treatment will eventually resume division and either continue to proliferate or die. Some drug-treated tumor cells undergo prolonged growth arrest and fail to resume cell division upon release from the drug.

Apoptosis is generally regarded as an active suicide response to various physiological or pathological stimuli. Recent studies have shown that a variety of DNA-damaging agents, including X-ray irradiation and several chemotherapeutic drugs (e.g. alkylating agents and topoisomerase II inhibitors) initiate pathways leading to apoptosis. The exact mechanism by which apoptosis is induced by these agents is not yet known. However, expression of the tumor suppressor gene p53 has been implicated in this process (Kwok and Sutherland, 1989, *J. Natl. Cancer Inst.* 81:1020-24; Kwok and Sutherland, 1991, *Int. J. Cancer* 49:73-76; Lane, 1992, *Nature* 358:15-16; Kuerbitz et al., 1992, *Proc. Natl. Acad. Sci. U.S.A.* 89:7491-95; Luo et al., 1995, *Nature* 375:159-61; Liu et al., 1996, *Cancer Res.* 56:31-35; Mellinghoff and Sawyers, 2000, *PPO Updates* 14: 1-11). In addition, the up-regulation of caspases (e.g., caspase 9 or caspase 3) or their chaperone molecules (e.g., heat shock protein 60) has been associated with apoptosis.

Cells can be rendered resistant to apoptosis in a variety of ways, including deletion of cellular genes such as the tumor suppressor gene PTEN, overexpression of active Ras, and overexpression of active PI3K. A particular cellular protein, AKT (the protein product of the c-akt gene) has been identified as a key regulator of cellular survival and an inhibitor of apoptosis, which has significant implications for oncogenesis and drug resistance. For example, the loss of PTEN correlates with increased AKT activity (Li et al., 1997, *Science* 275:1943-47; Liaw et al., 1997, *Nat. Genet.* 16:64-67; Nelen et al., 1997, *Hum. Mol. Genet.* 6:1383-87; Cantley and Neel, 1999, *Proc. Natl. Acad. Sci. U.S.A.* 96:4240-45; Datta et al., 1999, *Genes Dev.* 13:2905-27). In addition, suppression of apoptosis is not the only function that AKT may have in promoting oncogenesis. In some circumstances, AKT can also induce cell cycle progression. However, the observation that AKT can suppress apoptosis suggests that oncogenes may block adaptive cellular apoptosis by hyperactivating AKT.

Given the complexity of the apoptotic machinery, there are a number of pathways by which AKT might act to promote cell survival and inhibit cell death. AKT may block apoptosis by regulating expression or activity of members of Bcl-2 gene family (that are known to play a role in cell survival or cell death). Alternatively, AKT may regulate expression or activity of the caspase family of proteins, or the function of death receptor pathways. The regulatory effect of AKT may be through a direct mechanism—the phosphorylation of components of the apoptotic machinery, for example—or an indirect mechanism—such as by altering the expression level of genes that encode components of the death machinery. Recent studies suggest that AKT regulates apoptosis at multiple sites. A number of AKT targets, all playing critical roles in mediating cell death, have been identified, including BAD, caspase-9, the Forkhead family of transcription factors, and the NFκB regulator IKK (Datta et al., 1999, supra).

The c-kit proto-oncogene encodes a transmembrane tyrosine kinase growth factor receptor that is placed in the same class as the receptors for PDGF and CSF-1 by virtue of their similar immunoglobulin-like extracellular domains and the interruptions of their cytoplasmic tyrosine kinase domain by a hydrophilic insert. (Yarden et al., 1987, *EMBO J.* 6:3341-3351). Its ligand, known alternatively as stem cell growth factor ("SCF"), mast cell growth factor, kit ligand, or steel factor, is an early hematopoietic growth factor that, in conjunction with other growth factors, supports the proliferation and differentiation of multiple hematopoietic lineages. Id.

In several small-cell lung cancer cell lines and breast cancer cell lines, it has been demonstrated that co-expression of c-kit and SCF occurs, suggesting that autocrine growth stimulation may play a role in non-hematopoietic tumors. Autocrine growth requires co-expression of SCF and c-kit. In two independent studies, immunostaining of frozen sections using polyclonal antisera directed against the carboxyl terminus of c-kit has demonstrated uniformly strong staining of normal breast ductal epithelial cells. These studies also demonstrated that, using the same methodology, at least 10-20% of breast carcinomas retain c-kit expression. Neither of these studies, however, addressed the expression of SCF in breast tumors. It is possible, therefore, that the co-expression of c-kit and SCF could play a role in the growth regulation of some breast tumors. (Hines, et al., 1995, *Cell Growth & Differentiation*, 6:769-779; Natali et al., 1992, *Int. J. Cancer*, 52:713-717; Chui et al, 1996, *British J. of Cancer*, 73:1233-1236). In addition, co-expression of c-kit and other growth factors in breast cancer results in enhanced sensitivity to the EGF family of growth factors. (Hines et al., 1999, *Breast Cancer Research and Treatment* 58: 1-10).

Therefore, there exists a need in the art for improved detection of expression and activation of proteins and ligands that are directly or indirectly responsible for the expression or activation of AKT. There is also a need for improved detection of expression and activation of c-kit and expression of its ligand SCF.

SUMMARY OF THE INVENTION

This invention provides reagents and methods for identifying and detecting expression or activation of biological markers of tumorigenesis in cells and tissue samples from cancer patients. The methods provided herein are useful for predicting or assessing a response of an individual cancer patient to a particular treatment regimen, and methods useful for identifying efficacious anticancer compounds.

In a first aspect, the invention provides methods for assessing a response to administration of a chemotherapeutic or chemopreventive agent to an individual, comprising:
  (a) obtaining a first tissue or cell sample from the individual before exposing the individual to the chemotherapeutic or biological therapeutic agent;
  (b) obtaining a second tissue or cell sample from the individual after exposing the individual to the chemotherapeutic or biological therapeutic agent;
  (c) detecting the amount of one or a plurality of biological markers in the first tissue or cell sample and in the second tissue or cell sample;
  (d) comparing the amount of the one or a plurality of biological markers in said first tissue or cell sample with the amount in said second tissue or cell sample;
  (e) determining whether expression or activation of the one or a plurality of biological markers decreases following exposure to the chemotherapeutic or biological therapeutic agent when the amount of the one or a plurality of biological markers in the second tissue sample is less than the amount of the one or a plurality of biological markers in the first tissue sample;
wherein a response to the administration of a chemotherapeutic or biological therapeutic agent to an individual is assessed.

In certain embodiments, the one or a plurality of biological markers are expressed from tumor related genes. In other embodiments, the one or a plurality biological markers are cellular components of a tumor-related signaling pathway. In yet other embodiments, the biological markers are c-kit, SCF, pAKT, or pc-kit. In certain embodiments, the method of detecting the amount of the one or a plurality of biological markers comprises using an antibody or antibodies that are immunologically specific for the one or a plurality of biological markers. In other embodiments, the amount of one or a plurality of biological markers are determined immunohistochemically.

In yet other embodiments, the method of detecting the amount of one or a plurality of biological markers comprises,
  (a) staining the first and second tissue or cell samples using one or a plurality of antibodies detectably-labeled with an optical density label, wherein at least one antibody is immunologically specific for one or a plurality of biological markers, wherein the biological markers are c-kit, SCF, pAKT, or pc-kit; and
  (b) determining an optical density of the stained first and second tissue sample in subpart (a);
wherein said optical density corresponds to the amount of said one or a plurality of biological markers.

In other embodiments, the optical density is determined using image analysis. In further embodiments, the detectable label is a chromagen or a fluorophore. In yet further embodiments, the detectable label is DAB. In other embodiments, the agent is Glivac™.

In a second aspect, the invention provides methods for predicting the response to administration of a chemotherapeutic or chemopreventive agent to an individual, comprising:
  (a) obtaining a tissue or cell sample from the individual before exposing the individual to the chemotherapeutic or biological therapeutic agent;
  (b) detecting the amount of one or a plurality of biological markers in the tissue or cell sample;
  (c) comparing the amount of one or a plurality of biological markers determined in subpart (b) with the amount of one or a plurality of samples expressing known amounts of the markers in one or a plurality of control samples; and
  (e) determining the expression or activation level of the one or a plurality of biological markers compared with the expression or activation level markers in one or a plurality of control samples;
wherein a response to the administration of a chemotherapeutic or biological therapeutic agent to an individual is predicted based on the determination of decreased expression or activation level of the one or a plurality of biological markers.

In certain embodiments, the one or a plurality of biological markers are expressed from tumor related genes. In other embodiments, the one or a plurality biological markers are cellular components of a tumor-related signaling pathway. In yet other embodiments, the biological markers are c-kit, SCF, pAKT, or pc-kit. In certain embodiments, the method of detecting the amount of the one or a plurality of biological markers comprises using an antibody or antibodies that are immunologically specific for the one or a plurality of biological markers. In other embodiments, the amount of one or a plurality of biological markers are determined immunohistochemically.

In yet other embodiments, the method of detecting the amount of one or a plurality of biological markers comprises,
  (a) staining the first and second tissue or cell samples using one or a plurality of antibodies detectably-labeled with an optical density label, wherein at least one antibody is immunologically specific for one or a plurality of biological markers, wherein the biological markers are c-kit, SCF, pAKT, or pc-kit; and (b) determining an optical density of the stained first and second tissue sample in subpart (a);
wherein said optical density corresponds to the amount of said one or a plurality of biological markers.

In other embodiments, the optical density is determined using image analysis. In further embodiments, the detectable label is a chromagen or a fluorophore. In yet further embodiments, the detectable label is DAB. In other embodiments, the agent is Glivac™.

In a third aspect, the invention provides methods for identifying a compound as a chemotherapeutic or biological therapeutic agent, comprising:
(a) obtaining a first tissue or cell sample;
(b) obtaining a second tissue or cell sample;
(c) exposing the second tissue or cell sample to said compound;
(d) detecting the amount of one or a plurality of biological markers in the first tissue or cell sample and the second tissue or cell sample;
(e) comparing the amount of the one or a plurality of biological markers in said first tissue or cell sample and second tissue or cell sample;
(d) (f) determining whether expression or activation of the one or a plurality of biological markers decreases following exposure to said compound when the amount of the one or more biological markers in the second tissue or cell sample is less than the amount of the one or a plurality of biological markers in the first tissue or cell sample;
wherein the compound is identified as a chemotherapeutic or biological therapeutic agent.

In certain embodiments, the one or a plurality of biological markers are expressed from tumor related genes. In other embodiments, the one or a plurality biological markers are cellular components of a tumor-related signaling pathway. In yet other embodiments, the biological markers are c-kit, SCF, pAKT, or pc-kit. In certain embodiments, the method of detecting the amount of the one or a plurality of biological markers comprises using an antibody or antibodies that are immunologically specific for the one or a plurality of biological markers. In other embodiments, the amount of one or a plurality of biological markers are determined immunohistochemically.

In yet other embodiments, the method of detecting the amount of one or a plurality of biological markers comprises,
(a) staining the first and second tissue or cell samples using one or a plurality of antibodies detectably-labeled with an optical density label, wherein at least one antibody is immunologically specific for one or a plurality of biological markers, wherein the biological markers are c-kit, SCF, pAKT, or pc-kit; and
(b) determining an optical density of the stained first and second tissue sample in subpart (a);
wherein said optical density corresponds to the amount of said one or a plurality of biological markers.

In other embodiments, the optical density is determined using image analysis. In further embodiments, the detectable label is a chromagen or a fluorophore. In yet further embodiments, the detectable label is DAB.

This invention provides reagents and methods for detecting expression and activation of proteins and ligands that are directly responsible for inducing c-akt gene expression and/or activating AKT protein. Disclosed herein is the discovery that the c-kit proto-oncogene and its ligand, stem cell growth factor ("SCF" or "SCGF") are co-expressed in various amounts in breast cancers and that c-kit activation results in production of phosphorylated AKT (pAKT).

The invention also provides diagnostic methods for detecting and measuring c-kit, SCF, pc-kit and pAKT expression and protein levels and detecting and measuring their activation states for the treatment of tumors. The invention provides reliable assays for determining c-kit, SCF, pc-kit and pAKT protein levels and their activation state in cells or tissue samples obtained from patients that also permits a pathologist to exclude normal tissue from the analysis. Moreover, the invention provides methods for determining whether a cancer patient will benefit from a course of treatment using therapeutic agents directed at components of the c-kit signaling pathways. The invention further provides methods for monitoring a course of treatment using therapeutic agents directed at components of the c-kit signaling pathway. The invention also provides therapeutic agents identified by the inventive methods.

Specific embodiments of the present invention will become evident from the following more detailed description of certain preferred embodiments and the claims.

DESCRIPTION OF THE DRAWINGS

FIG. 1A shows a photomicrograph of the sample tissue immunohistochemically stained with an antibody immunohistochemically-specific for SCF, as described in Example 2, at 400× magnification using a technique described in Example 5. FIG. 1B shows the same breast cancer sample stained with an antibody to c-kit (400×), as described in Example 1. FIG. 1C shows a different field of the same cancer tissue stained for SCF (400×). FIG. 1D shows another field stained for c-kit (400×).

FIG. 2A is a tumor stained for pAKT. FIG. 2B show tumor sample 747 stained for c-kit. FIG. 2C shows sample 848 stained for SCF. FIGS. 2D and 2E are different fields of tumor sample 920 stained for either c-kit (FIG. 2D) or SCF (FIG. 2E).

DETAILED DESCRIPTION OF THE PREFERRED EMBODIMENTS

Figure 1A:
FIGS. 1A through 1D illustrate an immunohistochemical analysis of a human breast tissue sample identified by No. 12669b9.
Figure 1B:
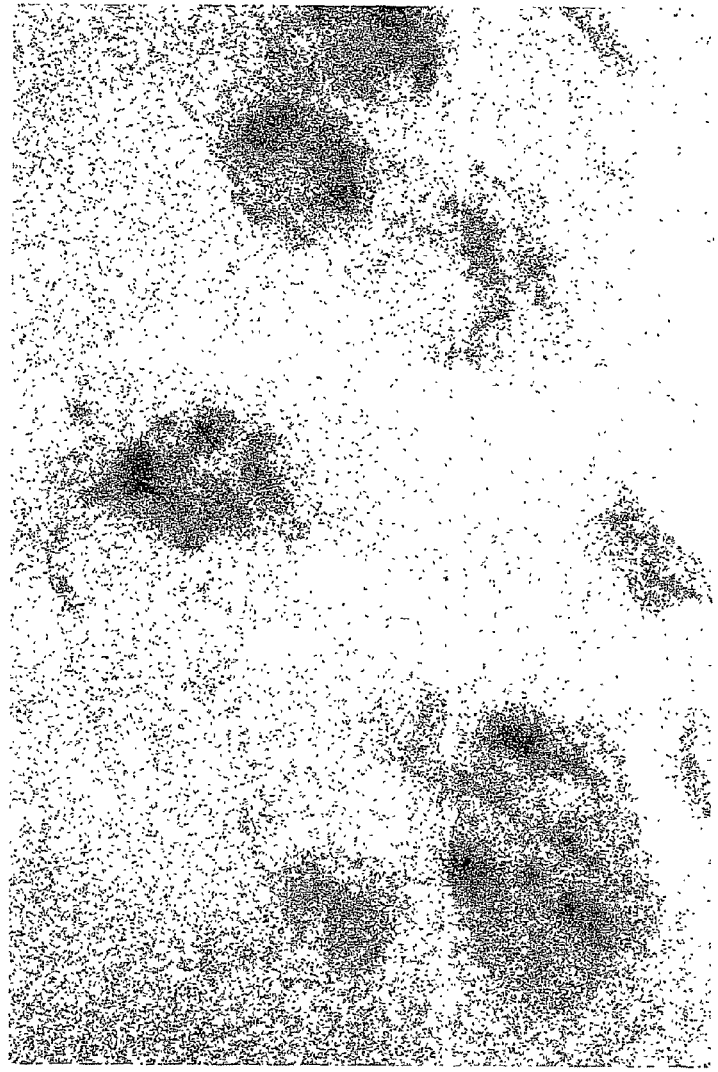
Figure 1C:
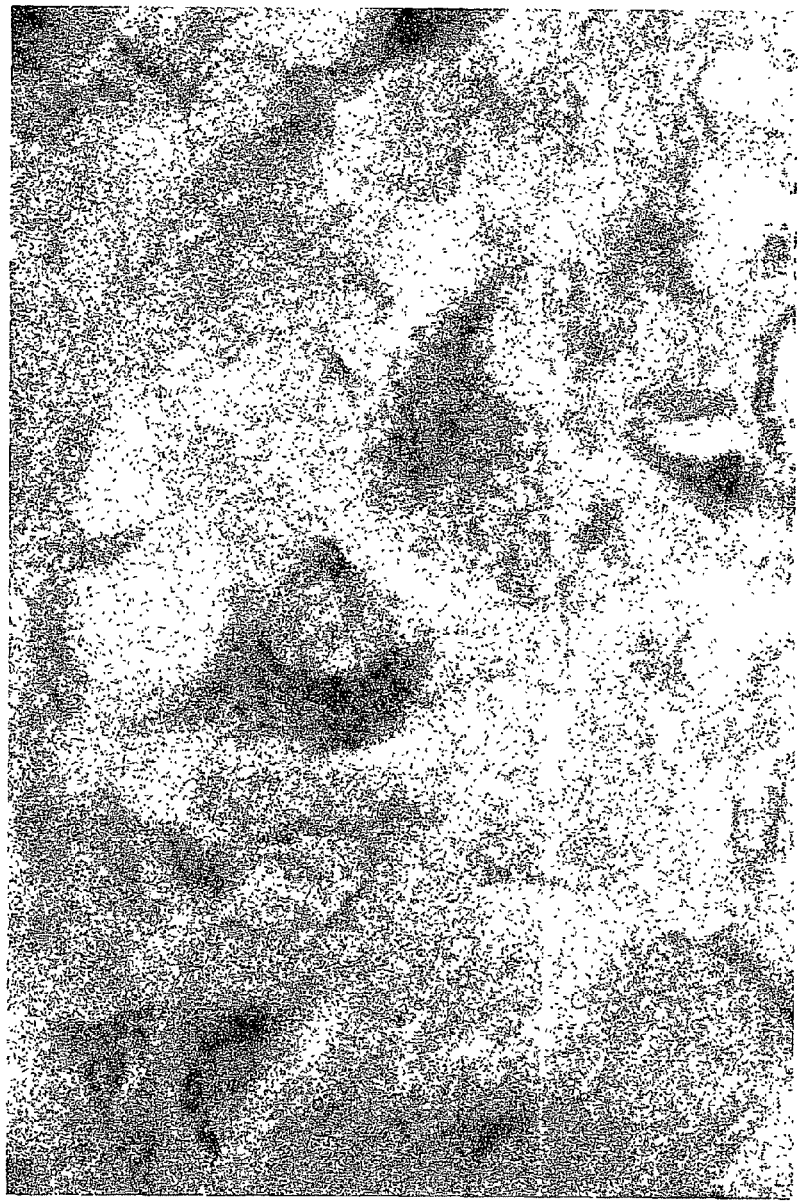
Figure 1D:
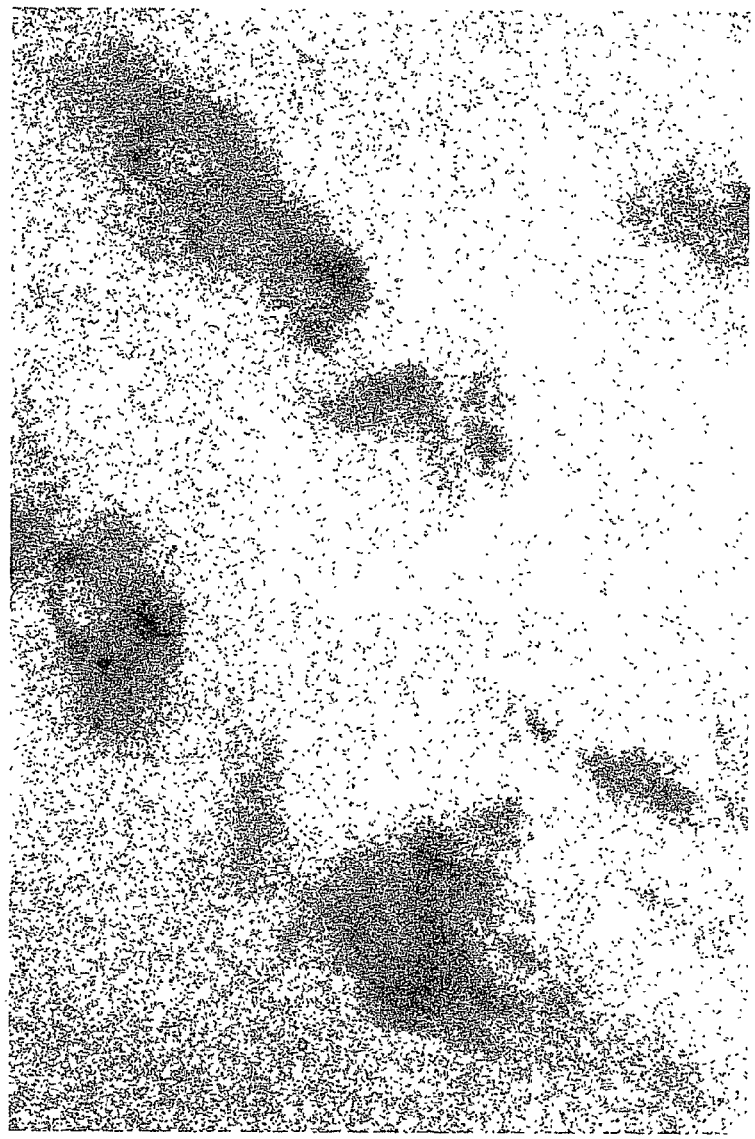

This invention provides methods for quantitatively determining expression and activation levels of tumor-related genes. The invention specifically provides methods for quantitatively determining expression and activation levels for cellular proteins encoded by c-kit, SCF and AKT, in tumor cells, including human tumor cells, as detected in cell or tissue samples from an individual.

c-kit and its ligand SCF are co-expressed in various amounts in breast and bladder cancers, and the downstream signal associated with the c-kit activation by SCF is phosphorylation of substrate AKT to phosphorylated AKT (pAKT). According to the invention, expression and activation of c-kit, SCF, and AKT are analyzed and monitored to identify patients that can benefit from treatment with a chemotherapeutic or biological therapeutic agent, to monitor patients treated with such agents, or to identify chemotherapeutic or biological therapeutic agents. For example, quantitative image analysis together with immunohistochemistry are used according to the invention to analyze expression of these three tumor markers, in order to identify patients that can benefit from treatment with a chemotherapeutic or biological therapeutic agent, including but not limited to tyrosine kinase inhibitors. In particular embodiments, such tyrosine kinase inhibitors include but are not limited to STI-571, which is known to inhibit c-kit kinase. (Drucker, 2001, *Am. Soc. Of Clinical Oncology,* 2001 Educational Book 37th Annual Meeting, San Francisco, Calif.).

In contrast to traditional anticancer methods, where chemotherapeutic drug treatment is undertaken as an adjunct to and after surgical intervention, neoadjuvant (or primary) chemotherapy consists of administering drugs as an initial treatment in cancer patients. One advantage of such an approach is that, for primary tumors of more than 3 cm, it permits the use of conservative surgical procedures (as opposed to, e.g. radical mastectomy in breast cancer patients) for the majority of patients. Another advantage is that for many cancers, a partial and/or complete response is achieved in about two-thirds of all cases. Finally, because the majority of patients are responsive after two to three cycles of chemotherapeutic treatment, it is possible to monitor the in vivo efficacy of the chemotherapeutic regimen employed, which is important for a timely identification of those cancers which are non-responsive to chemotherapeutic treatment. Timely identification of non-responsive tumors, in turn, allows the clinician to limit the cancer patient's exposure to unnecessary side-effects of treatment and to institute alternative treatments. However, the methods present in the art, including histological examination, are insufficient for such a timely and accurate identification. The present invention provides methods by which a more informed and effective region of therapy can be administered. In addition, the present invention provides methods by which the responsiveness or non-responsiveness of a therapy regimen can be assessed, thereby limiting the patient's exposure to the chemotherapeutic drug.

A cancer diagnosis, both initial diagnosis of disease and subsequent monitoring of the disease course, before, during, or after treatment, is conventionally confirmed through histological examination of cell or tissue samples removed from a patient. Clinical pathologists need to be able to accurately determine whether such samples are benign or malignant and to classify the aggressiveness of tumor samples deemed to be malignant, because these determinations often form the basis for selecting a suitable course of patient treatment. Similarly, the pathologist needs to be able to detect the extent to which a cancer has grown or gone into remission, particularly as a result of or consequent to treatment, most particularly treatment with chemotherapeutic or biological agents.

Histological examination traditionally entails tissue-staining procedures that permit morphological features of a sample to be readily observed under a light microscope. A pathologist, after examining the stained sample, typically makes a qualitative determination of whether the tumor sample is malignant. It is difficult, however, to ascertain a tumor's aggressiveness merely through histological examination of the sample, because a tumor's aggressiveness is often a result of the biochemistry of the cells within the tumor, such as protein expression or suppression and protein activation, which may or may not be reflected by the morphology of the sample. Therefore, it is important to be able to assess the biochemistry of the cells within a tumor sample. Further, it is desirable to be able to observe and quantitate both gene expression and protein activation of tumor related genes or proteins, or more specifically cellular components of a tumor-related signally pathway.

Automated (computer-aided) image analysis systems known in the art can augment visual examination of samples. In a representative system, the cell or tissue sample is exposed to detectably labeled reagents specific for a particular biological marker, and the magnified image of the cell is then processed by a computer that receives the image from a charge-coupled device (CCD) or camera such as a television camera. Such a system can be used, for example, to detect and measure expression and activation levels of the c-kit, SCF, pc-kit, and pAKT in a sample. This methodology provides more accurate diagnosis of cancer and a better characterization of gene expression in histologically identified cancer cells, most particularly with regard to expression of tumor marker genes or genes known to be expressed in particular cancer types and subtypes (i.e., different degrees of malignancy). This information permits a more informed and effective regimen of therapy to be administered, because drugs with clinical efficacy for certain tumor types or subtypes can be administered to patients whose cells are so identified. A non-limiting example is administration of tyrosine kinase inhibitors to patients having tumor biopsy or other test samples that test positive for c-kit, SCF, pc-kit, and pAKT.

Another drawback of conventional anticancer therapies is that the efficacy of specific chemotherapeutic agents in treating a particular cancer in an individual human patient is unpredictable. In view of this unpredictability, the art is unable to determine, prior to starting therapy, whether one or more selected agents would be active as anti-tumor agents or to render an accurate prognosis of course of treatment in an individual patient. This is especially important because the same clinical cancer may present the clinician with a choice of treatment regimens, without any current way of assessing which regimen will be most efficacious for a particular individual. It is an advantage of the methods of this invention that they are able to better assess the expected efficacy of a proposed therapeutic agent (or combination of agents) in an individual patient. Additional features of the claimed methods for assessing the efficacy of chemotherapeutic regimens are that they are both time- and cost-effective and minimally traumatic to cancer patients.

In the practice of one embodiment of the methods of this invention, a two-component immunohistochemical staining system is used. In this embodiment, cell pellets or tissues are counterstained with a dye, stain or detectable label producing a first color while proteins of interest in the cell pellet or tissue sample are stained with a dye, stain or detectable label producing a second, different color. The image of the cells in the cell pellet and tissue sample is then magnified in a light microscope and split into a pair of separated images. A pair of optical filters that are specifically matched to have a maximum absorption for each specific stain is used to enhance the separated images. One of the optical filters preferentially transmits light having a wavelength at the absorption wavelength of the counterstained tissue. The other, preferably narrow bandpass optical filter preferentially transmits light in the regions of spectral absorption for the dye, stain or detectable label used to detect the protein of interest. Using image analysis filters, different cellular proteins in various components, such as the membrane, cytoplasm and nucleus, can be quantified. For optimal results, the imaging system is calibrated prior to taking any measurements.

One of the advantages of the use of methods of this invention that utilize two-component immunohistochemical staining is that the subcellular localization of a protein of interest can be determined.

In the practice of another embodiment of the methods of the invention, the amount of target protein in a biological sample is quantitated (i.e., the amount of target protein is measured) using calibration curves that relate the amount and degree of target protein-specific staining to the amount of the target protein in the sample. This is most generally accomplished by comparing experimental or patient samples with cell samples prepared using cells, most preferably cultured cell lines that produce a consistent amount of the target protein that can be determined with high degrees of accuracy and precision. In certain preferred embodiments, a plurality of cell populations are assayed that each express different amounts of the target protein, to permit a calibration curve to be produced relating staining intensity with amount of protein in a sample. Such cell populations are used to determine the amount of target protein-specific staining associated with varying amounts of target protein in the different cell populations. In certain preferred embodiments the amount of target protein-specific staining is normalized or expressed relative to the amount of total cell protein, to provide a convenient measure for analyzing biological tissues, preferably tumor tissue and most preferably malignant tumor tissue, in which a determination of cell number would be impractical or unreliable. In the practice of the invention, the correlation between target protein-specific staining and the amount of target protein expressed in a cell is expressed as a calibration curve relating the amount of target protein to a physical parameter, most preferably optical density, associated with target protein-specific staining. The calibration curves produced according to and used with the methods of the invention are also advantageously expressed as an algorithm, most preferably in the form of a linear or logarithmic equation, and are preferably automated, for example, by programming a device such as a computer to convert a sample staining intensity to an amount of a target protein in the sample.

In the practice of another embodiment of the methods of the invention, the subcellular localization of a protein of interest can be determined. This is advantageous because some proteins, such as the estrogen receptor, are localized in the cytoplasm of the cell until they are activated, at which point they translocate into the nucleus where they can participate in, for example, gene expression.

A description of exemplary procedures for quantitative immunohistochemical image analysis of tissue samples can be found, generally, in co-pending U.S. patent application Ser. Nos. 09/760,120 and 09/760,121, both filed Jan. 12, 2001, and WO 01/51924 and WO 01/51928, both filed Jan. 12, 2001, all of which are incorporated herein by reference in their entirety. As an example, Quantitative image analysis was performed on a Cell Analysis Systems Model 200, available from Becton Dickinson Company, Mountain View, Calif. Quantitative image analysis, as encompassed by this invention, can be performed on systems from other vendors, such as, but not limited to, ChromaVision Medical Systems (San Juan Capistrano, Calif.).

In the practice of the methods of this invention, target proteins including but not limited to c-kit, SCF, pc-kit, and pAKT can be detected using a specific reagent, most preferably an antibody, that is itself detectably labeled, or using an unlabeled, target protein-specific antibody and a second antibody that is detectably labeled and recognizes the target protein-specific antibody. Alternatively, any molecule that can be detectably labeled and that specifically binds to the target protein can be used in the practice of the methods of the invention. In a preferred embodiment of the methods of the present invention, a two-component immunohistochemical staining system is used to differentially stain the target protein and the tissue or cell sample so that the stained target protein can be more readily distinguished from the counterstained tissue or cell sample. Following immunohistochemical staining, the optical image of the tissue or cell sample preferably generated by a computer-aided image analysis system is then magnified under a light microscope and separated into a pair of images. The separated images are enhanced using a pair of optical filters, one having a maximum absorption corresponding to the stain and the other having a maximum absorption corresponding to the counterstain, thereby providing an optimum discrimination between the two stains. In other embodiments of the method of the present invention, a plurality of image analysis filters are used to detect, differentiate, and quantitate staining levels of different cellular proteins in various components (e.g., membrane, cytoplasm, and nucleus). In a non-limiting example, the target can be stained using diaminobenzidine (DAB) and the tissue or cell sample can be counterstained using ethyl green or methylene blue.

It will be recognized by those with skill in the immunohistochemistry arts that dye lot variations and variability in certain environmental conditions, such as relative humidity can affect results obtained at different times using the methods of the invention. In certain embodiments of the methods of the present invention, stain and counterstain lot variability is controlled by using the same reagents to stain the sample cells and first and second control cell pellets. In other certain embodiments of the methods of the present invention, environmental differences and variability in the staining procedure are controlled for by staining the sample cells and first and second control cell pellets at the same time.

In certain embodiments, target protein-specific staining is detected, measured and quantitated using image analysis equipment, defined herein as comprising a light or fluorescence microscope, an image-transmitting camera and a view screen, most preferably also comprising a computer that can be used to direct the operation of the device and also to store and manipulate the information collected, most preferably in the form of optical density of certain regions of a stained tissue preparation. Image analysis devices useful in the practice of this invention include but are not limited to the CAS 200 system (Becton Dickenson, Mountain View, Calif.).

In certain embodiments, the inventive methods are practiced using such an image analysis system as follows. After immunohistochemical staining as described above, a quantified measure of the percentage of expressing cells can be taken by digitizing microscope images of stained samples, and converting light intensity values in each picture element (pixel) of the digitized image to optical density values, which correspond to the percentage of stained cell components (such as nuclei). More specifically, computerized image analysis can be used to determine a quantity of cells having a particular stain using a digital grey scale image. Grey scale images are representative of the amount of an optical enhancement factor, such as a chromagen, which binds to a specific target under study and thereby allows optical amplification and visualization of the target.

As used in the practice of the methods of this invention, a computerized image analysis apparatus includes a means such as a lens for magnifying and displaying the image of a group of cells of a specimen from a field on a microscope slide. The specimen cell population is prepared using staining and counterstaining techniques known in the immunohistochemical arts, such as enzymatic staining methods and chemical staining methods. Appropriate stains and counterstains are selected by their ability to enable cells to be distinguished, inter alia, those that contain antibody sandwich complexes comprising specific enzymes or markers and those that do not contain such complexes, through cameras used with the computerized image analysis system. After staining, the image field is digitized by the apparatus and stored in a memory provided by the system. From the digitized image, a nuclear or cytoplasmic image mask is formed by using one wavelength of light such as red wavelength or green optical filter for form the image. The tissue mask is stored and a second filter is used to form another filtered image of the same areas with the optical enhancement factor. Differentiation of cellular characteristics can be made by comparing the first image with the second image to obtain a quantification of material stained with the optical enhancement factor and thus, an assay of the amount of the particular target under study.

In a first step, any expressed target protein in the cells is identified by adding a detectably-labeled primary antibody specific for the target protein, or alternatively an unlabeled primary antibody and a detectably-labeled secondary antibody specific for the primary antibody. The antibodies are incubated with the sample for a time to form complexes if these antigens are present. The complexes are then visualized, either by directly detecting the label, or, if the detectable label is an enzyme, incubating the sections with a compound, such as a chromagen under appropriate conditions. As an example, the primary antibody can be labeled peroxidase, with the subsequent use of the chromagen DAB. In a second step, the tissue is counterstained with another optical enhancement factor, such as, but not limited to ethyl green. Although a staining technique using peroxidase and ethyl green is exemplary, other stains and optical enhancement factors are also suitable. For example, other chromagens can be used with peroxidase, including, but not limited to 3-Amino-9-Ethylcarbazole (AEC), which produces a red color, and 4-Chloro-1-Naphthol. In addition, other enzymes that can be used to label the primary antibody are encompassed by this invention, including, but not limited alkaline phosphatase. Examples of chromagens that can be used with alkaline phosphatase include, but are not limited to Fast Red, Fast Green, and 5-bromo-4-chloro-3-indolyl phosphate/nitroblue tetrazolium (BCIP/NBT). In addition, the use of florescent dyes is encompassed by methods of the present invention. As non-limiting examples of florescent dyes, the use of Fluorescein (fluoroisothiocyanate or FITC) and Rhodamine.

Further, the use of ethyl green is exemplary of counter stains, but use of other counter stains are encompassed by the methods of the present invention. For example, a non-limiting list of additional counter stains include hematoxylin, fast red, methyl green. A counter stain is chosen for a particular stain based on the spectral separation that can be achieved such that filtering at two wavelengths can be achieved. For example, ethyl green offers good spectral separation from the DAB precipitate, as described in more detail below. Other examples of pairs of stains/counter stains that offer good spectral separation include, but are not limited to, Fast Red and Hematoxylin, AEC and Hematoxylin, and FITC and Texas Red. Those skilled in the art will recognize that this list of stains and counter-stain is merely exemplary and, therefore, does not serve to limit the invention.

As an example of the an embodiment of a method of the present invention, spectral studies have shown that the ethyl green stain offers good spectral separation from the DAB precipitate produced by immunoperoxidase and permits different features of the image to be readily separated by filtering the image at two different wavelengths. This allows the image to be digitized into two separate images, for example, one in which all the cell nuclei are optically enhanced (using, for example, ethyl green or Fast Green) and one in which only those tissue areas with receptor staining (DAB) are optically enhanced. The resulting tissue preparation stained with ethyl green will have green nuclei with varying degrees of brown DAB precipitate localized to the cytoplasm or nuclei, proportional to the level of expression of the marker protein. Although a staining technique using peroxidase and ethyl green is described, other stains and optical enhancement factors are also suitable (such as alkaline phosphatase coupled with a specific chromagen such as Fast Red or Fast Green counterstain). Spectral studies have shown that the ethyl green stain offers good spectral separation from the DAB precipitate of the immunoperoxidase technique such that filtering at two different wavelengths can readily separate different features of the image. This allows the image to be digitized into two separate images, one in which all the cell nuclei are optically enhanced (ethyl green or Fast Green) and one in which only those tissue areas with receptor staining (DAB) are optically enhanced. In a particular embodiment, the images can be separated by a 600 nanometer (red) filter to produce an image of the counterstained area and a 500 nanometer (green) filter to produce an image of the tissue areas staining with the DAB precipitate.

To further differentiate the stained areas, an interactive threshold setting technique can be used where an operator visualizing the images can set a boundary on the areas under consideration. When such boundaries are set, images are formed by eliminating all parts of the image that are below the thresholds in optical density. As practiced according to the teachings contained herein, a threshold is advantageously set for the first image, and a second threshold is set for the second image.

Further, the image processing method performed preferably using the image analysis systems of the invention comprises first forming a mask image of the tissues under consideration with, for example, a red filter. This mask image is stored, preferably in the system's computer memory and another image for expressed protein quantification is acquired by using, for example, a green-filtered version of the same image. The effect of the filters in combination is to optically enhance (i.e., make darker) those areas of the tissue mask where tissue components are stained with DAB and to make lighter those tissue components stained only with the green counterstain. An image analysis can then be performed using only those areas of the image that are stained and are within the mask.

The combination of red and green optical filters and DAB and ethyl green or other green counterstains are advantageously used in the practice of the methods of the invention. This combination provides a convenient and advantageous way to discriminate between two counterstained areas. Those with skill in the art will recognize that there are a plurality of other stains, filters, staining or optical enhancement methods and filtering methods that can be used to optically enhance one particular area or feature over another cell feature, such as Fast green, eosin.

For example, expression and activation of proteins expressed from tumor-related genes can be detected and quantitated using methods of the present invention. Further, expression and activation of proteins that are cellular components of a tumor-related signaling pathway can be detected and quantitated using methods of the present invention. Further, proteins associated with breast cancer can be quantified by image analysis using a suitable primary antibody against Her-1, Her-2, p-Her-1, p-Her-2, p-ERK, c-kit, p-AKT, or SCF, or to their phosphorylated forms, and a secondary antibody (such as rabbit anti-mouse IgG when using mouse primary antibodies) and/or a tertiary avidin (or Strepavidin) biotin complex ("ABC"). Examples of reagents include a rabbit polyclonal antibody specific for pAKT and obtained from Cell Signaling Technology (Beverly, Mass., Cat. No. 9277); anti-SCF antibody, obtained from Santa Cruz Biotechnology (Santa Cruz, Calif., Cat. No. SC-9132); and a polyclonal anti-c-kit antibody obtained from Neomarkers, Inc. (Fremont, Calif., Cat. No. RB-1518).

In practicing the method of the present invention, staining procedures can be carried out by a technician in the laboratory. Alternatively, the staining procedures can be carried out using automated systems.

The amount of target protein can then be quantitated by the average optical density of the stained antigens. Also, the proportion or percentage of total tissue area stained may be readily calculated, as the area stained above an antibody threshold level in the second image. Following visualization of nuclei containing c-kit, SCF, and pAKT, the percentage or amount of such cells in tissue derived from patients after treatment may be compared to the percentage or amount of such cells in untreated tissue.

From these comparisons, the potential effectiveness of a putative therapeutic or chemopreventive agent against a tumor can be determined. Specifically, if there is a greater amount of expression and activation of protein expressed from a tumor-related gene in the untreated portion of the sample than there is in the treated portion of the sample, then the therapeutic agent used in the treatment will be predicted to be an effective agent for treating the cancer. Further, if there is a greater amount of expression and activation of protein that is a cellular component of a tumor-related signaling pathway in the untreated portion of the sample than there is in the treated portion of the sample, then the therapeutic agent used in the treatment will be predicted to be an effective agent for treating the cancer. Further, if there is a greater amount of expression and activation of c-kit, SCF, and pAKT in the untreated portion of the sample than there is in the treated portion of the sample, then the therapeutic agent used in the treatment will be predicted to be an effective agent for treating the cancer. Conversely, if there is a substantially equal percentage of cells expressing c-kit, SCF, and pAKT in both the treated and untreated portions of the sample, or there is less protein expression in the untreated portion of the sample, then the putative therapeutic agent will not be predicted to be effective for treatment of the cancer. For example, this procedure can be used to establish that a c-kit tyrosine kinase inhibitor, Novartis agent STI-571 (GLIVEC™), is predicted to be a potentially effective agent for treating a cancer sample.

Particularly useful embodiments of the present invention and the advantages thereof can be understood by referring to Examples 1-7. These Examples are illustrative of specific embodiments of the invention, and various uses thereof. They are set forth for explanatory purposes only, and are not to be taken as limiting the invention.

Example 1

Staining Procedure for c-Kit

Staining for c-kit was performed on a Benchmark™ automated staining module (Ventana Medical Systems, Inc., Tucson, Ariz.) using a polyclonal antibody to c-kit (Neo-Markers, Fremont, Calif.). 10% Neutral Buffered Formalin fixed 4 micron paraffin sections of the sample were place onto coated slides. The Benchmark bar-code specific for the c-kit staining protocol was placed onto the slide and the slide placed onto the Benchmark. All subsequent steps, drying, deparaffinization antigen retrieval (Cell Conditioning 1 mM EDTA), and detection were performed automatically by the Benchmark. All test reagents are available from Ventana Medical Systems, including the I-View DAB Detection Kit, unless otherwise noted. The protocol implemented in using the automated system is described in Table 1. Where indicated, one drop is one reagent dispense. The sample was then manually counterstained with 4% Ethyl Green 0.1 M pH 4 acetate buffer for 10 minutes. The results of staining for c-kit are described below in Example 5.

TABLE I

| | |
|---|---|
| 1 | **Select EZ Prep** |
| 2 | ****Start Timed Steps |
| 3 | **Mixers Off** |
| 4 | Warmup Slide to 75° C., and Incubate for 4 minutes |
| 5 | Apply EZPrep Volume Adjust |
| 6 | Incubate for 4 minutes |
| 7 | Rinse Slide + |
| 8 | Apply EZPrep Volume Adjust |
| 9 | Incubate for 4 minutes |
| 10 | Rinse Slide + |
| 11 | Apply EZPrep Volume Adjust |
| 12 | Apply Coverslip |
| 13 | Warmup Slide to 76° C., and Incubate for 4 minutes |
| 14 | Rinse Slide + |
| 15 | Apply Depar Volume Adjust |
| 16 | Apply Coverslip |
| 17 | Warmup Slide to 42° C., and Incubate for 2 minutes |
| 18 | **Mixers On** |
| 19 | Rinse Slide + |
| 20 | Apply Medium Cell Conditioner #1 |
| 21 | Apply CC Long Coverslip |
| 22 | Warmup Slide to 95° C., and Incubate for 8 minutes |
| 23 | Apply Medium Cell Conditioner #1 |
| 24 | Apply Coverslip |
| 25 | Warmup Slide to 100° C., and Incubate for 4 minutes |
| 26 | Apply Coverslip |
| 27 | Apply Cell Conditioner #1 |
| 28 | Incubate for 4 minutes |
| 29 | Apply Coverslip |
| 30 | Apply EZPrep CC Volume Adjust |
| 31 | Incubate for 4 minutes |
| 32 | Apply Coverslip |
| 33 | Apply Medium Cell Conditioner #1 |
| 34 | Incubate for 4 minutes |
| 35 | Apply Coverslip |
| 36 | Apply Cell Conditioner #1 |

TABLE I-continued

| | |
|---|---|
| 37 | Incubate for 4 minutes |
| 38 | Disable Slide Heater |
| 39 | Incubate for 8 minutes |
| 40 | Rinse Slide + |
| 41 | Adjust Slide Volume |
| 42 | Apply Coverslip |
| 43 | **Select Reaction Buffer** |
| 44 | Warmup Slide to 42° C., and Incubate for 2 minutes |
| 45 | Rinse Slide + |
| 46 | Adjust Slide Volume |
| 47 | Apply One Drop of I-VIEW INHIBITOR, Apply Coverslip, and Incubate 4 min. |
| 48 | Rinse Slide + |
| 49 | Adjust Slide Volume |
| 50 | Apply One Drop of c-kit primary antibody [PREP KIT 4], Apply Coverslip, and Incubate 32 min. |
| 51 | Rinse Slide + |
| 52 | Adjust Slide Volume |
| 53 | Apply One Drop of I-VIEW BIOTIN Ig, Apply Coverslip, and Incubate 8 min. |
| 54 | Rinse Slide + |
| 55 | Adjust Slide Volume |
| 56 | Apply One Drop of I-VIEW SA-HRP, Apply Coverslip, and Incubate 8 min. |
| 57 | Rinse Slide + |
| 58 | Adjust Slide Volume |
| 59 | Apply Coverslip |
| 60 | Rinse Slide + |
| 61 | Adjust Slide Volume |
| 62 | Apply One Drop of I-VIEW DAB and One Drop I-VIEW $H_2O_2$, Apply Coverslip, and Incubate 8 min. |
| 63 | Rinse Slide + |
| 64 | Adjust Slide Volume |
| 65 | Apply One Drop of I-VIEW COPEER, Apply Coverslip, and Incubate 4 min. |
| 66 | Rinse Slide + |

Example 2

Staining Procedure for SCF

SCF staining was performed using a polyclonal antibody to SCF (Santa Cruz Biotechnology, Santa Cruz, Calif.). A biotinylated anti-rabbit secondary antibody (Jackson Research Labs, West Lake, Pa.). the "StreptABComplex-HRP" (Streptavidin/Biotin Complex with a Horseradish Peroxidase) label kit (DAKO Corporation, Carpinteria, Calif.), and the DAB chromagen (Dako) were used as the detection system for SCF. 10% Neutral Buffered Formalin fixed 4 micron paraffin sections of the sample were place onto coated slides. To prepare the sample for staining, the sample was first deparaffinized and hydrated to water. Antigen retrieval was preformed enzymatically with Digest-All 1 (Zymed Labs), a Ficin digestion solution. 1-2 drops of the manufacture's ready-to-use solution was added to the sections and incubated for 20 minutes at 37° C. The sections were then washed well with deionized water and rinsed with TBS. Endogenous peroxidase was blocked by incubating the sections with a 3% hydrogen peroxide/methanol solution for 10 minutes, followed by a deionized water wash. The sections were then blocked using 10% blocking goat serum in 0.1% BSA/0.1% Triton X for 10 minutes. The goat serum was then shaken off.

The sections were incubated with a 1:20 dilution of SCF primary antibody at 37° C. for 45 minutes. The StreptABC label was prepared while the primary antibody was incubating with the sections by adding 4 μls of Streptavidin solution with 4 μls biotin solution in 1 ml of 50 mM Tris-HCL buffer, pH 7.6. After SCF primary antibody incubation, the sections were washed well with TBS and incubated with a 1:300 dilution of biotinylated Goat anti-rabbit IgG at 37° C. for 20 minutes. The sections were washed well with TBS, followed by incubation with the StreptABC label at 37° C. for 20 minutes. The sections were washed well with TBS, and DAB liquid chromagen was applied at room temperature for 5 minutes. The sections were then washed well with deionized water. The slides were counterstained with 4% ethyl green. The results of staining for SCF are described below in Example 5.

Example 3

Staining Procedure for Phospho-AKT p-AKT staining was performed using a Dako Autostainer with the LSAB2 kit (described above). 10% Neutral Buffered Formalin fixed 4 micron paraffin sections of the sample were place onto coated slides. To prepare the sample for staining, the sample was first deparaffinized and hydrated to water. Antigen retrieval was preformed with 0.1 M citrate retrieval buffer, pH 6.0 in a Decloaker Chamber (Biocare Medical, Walnut Grove, Calif.) following the manufacturer's instructions. The sections were allowed to cool for 15 minutes, and then washed well with deionized water. Endogenous peroxidase was blocked by incubating the sections with a 3% hydrogen peroxide/Methanol solution for 10 minutes, followed by a deionized water wash. The sections were then blocked using 10% blocking goat serum in 0.1% BSA/0.1% Triton X for 10 minutes. The goat serum was then shaken off.

The sections were then incubated with a 1:75 dilution of p-AKT primary antibody (Cell Signaling Technology, Beverly, Mass.) at 4° C. overnight. The next morning, the sections were removed from the refrigerator and allowed to come to room temperature, about 30 minutes. The slides were washed well with TBS and loaded into the Dako Autostainer. The Autostainer was programmed to apply the biotinylated link for 30 minutes, the streptavidin-HRP reagent for 30 minutes, and the DAB chromagen for 5 minutes. The slides were rinsed with TBS/Tween by the autostainer between the linking antibody, labeling, and DAB chromagen applications. After DAB chromagen, the slides were removed from the autostainer and washed well with deionized water. The slides were counterstained with 4% ethyl green. The results of staining for SCF are described below in Example 5

Example 4

Staining Procedure for Phospho-KIT pc-kit staining was performed using a Dako Autostainer with a reagent kit obtained from DAKO Corp. (the LSAB2 kit (labeled streptavidin-biotin) containing a Horseradish Peroxidase Label). 10% Neutral Buffered Formalin fixed 4 micron paraffin sections of the sample were place onto coated slides. To prepare the sample for staining, the sample was first deparaffinized and hydrated to water. Antigen retrieval was preformed with 1 mM EDTA in a Decloaker Chamber (Biocare Medical, Walnut Grove, Calif.), an electric pressure cooker that can be utilized for heat-induced epitope retrieval (HIER) procedures, following the manufacturer's instructions. The sections were allowed to cool for 15 minutes, and then washed well with deionized water. Endogenous peroxidase was blocked by incubating the sections with a 3% hydrogen peroxide/methanol solution for 10 minutes, followed by a deionized water wash. The sections were then blocked using 10% blocking goat serum in 0.1% BSA/0.1% Triton X for 10 minutes. The goat serum was then shaken off.

The sections were then incubated with a 1:50 dilution of p-kit (Try 719) primary antibody (Cell Signaling Technology, Beverly, Mass.) at 4° C. overnight. The next morning, the sections were removed from the refrigerator and allowed to come to room temperature, about 30 minutes. The slides were washed well with TBS and loaded into the Dako Autostainer. The Autostainer was programmed to apply the biotinylated link for 30 minutes, the streptavidin-HRP reagent for 30 minutes, and the DAB chromagen for 5 minutes. The slides were rinsed with TBS/Tween by the autostainer between the linking antibody, labeling, and DAB chromagen applications. After DAB chromagen, the slides were taken off the autostainer and washed well with deionized water. The slides were counterstained with 4% ethyl green. The result was the ability to detect the level of expression or activation of pc-kit in the sample (data not shown).

Example 5

Immunohistochemical Staining of Tumor Sample for c-kit, SCF, and pAKT

To identify a patient to be a candidate for c-kit inhibitors, such as Novartis' Glivec™, tumor samples were examined for c-kit and SCF expression. Paraffin blocks of tumor samples were sectioned at 4-5 microns and the sections were placed onto coated slides. The slides were then stained as described above for either c-kit, SCF, or pAKT. The results of these experiments are represented in FIGS. 1A through 1D. These Figures represent microphotographs of one individual's breast cancer sample. Two microphotographs (FIGS. 1A and 1C) represent fields stained with antibodies to SCF and two microphotographs (FIGS. 1B and 1D) represent fields stained with antibodies to c-kit. All photographs show staining and thus that the same tumor expresses both c-kit and SCF. Therefore, this breast cancer sample identified the patient as a good candidate for c-kit inhibitors.

Figure 2A:
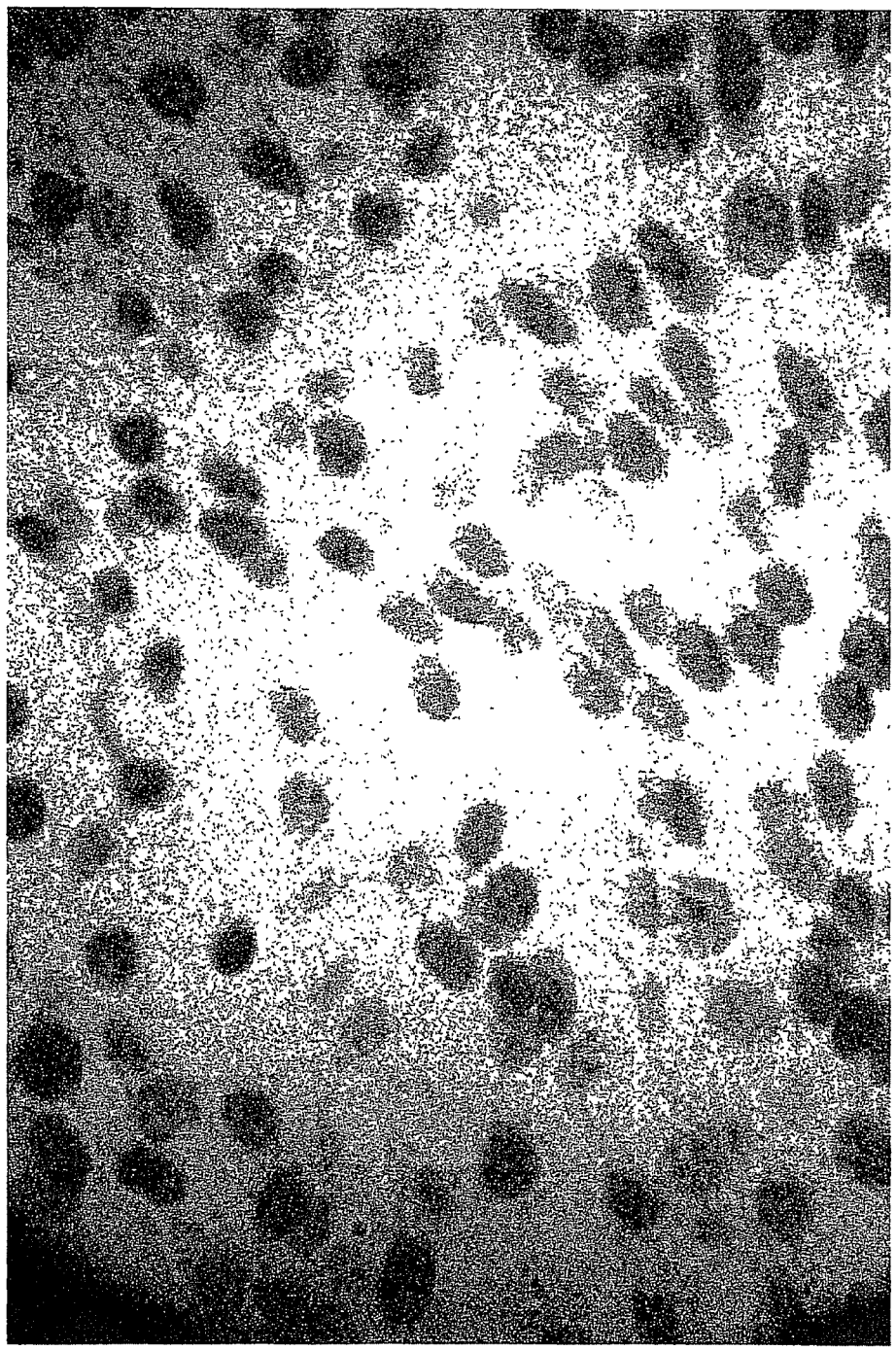
FIGS. 2A through 2E show the results of immunohistochemical analyses of tumor samples.
Figure 2B:
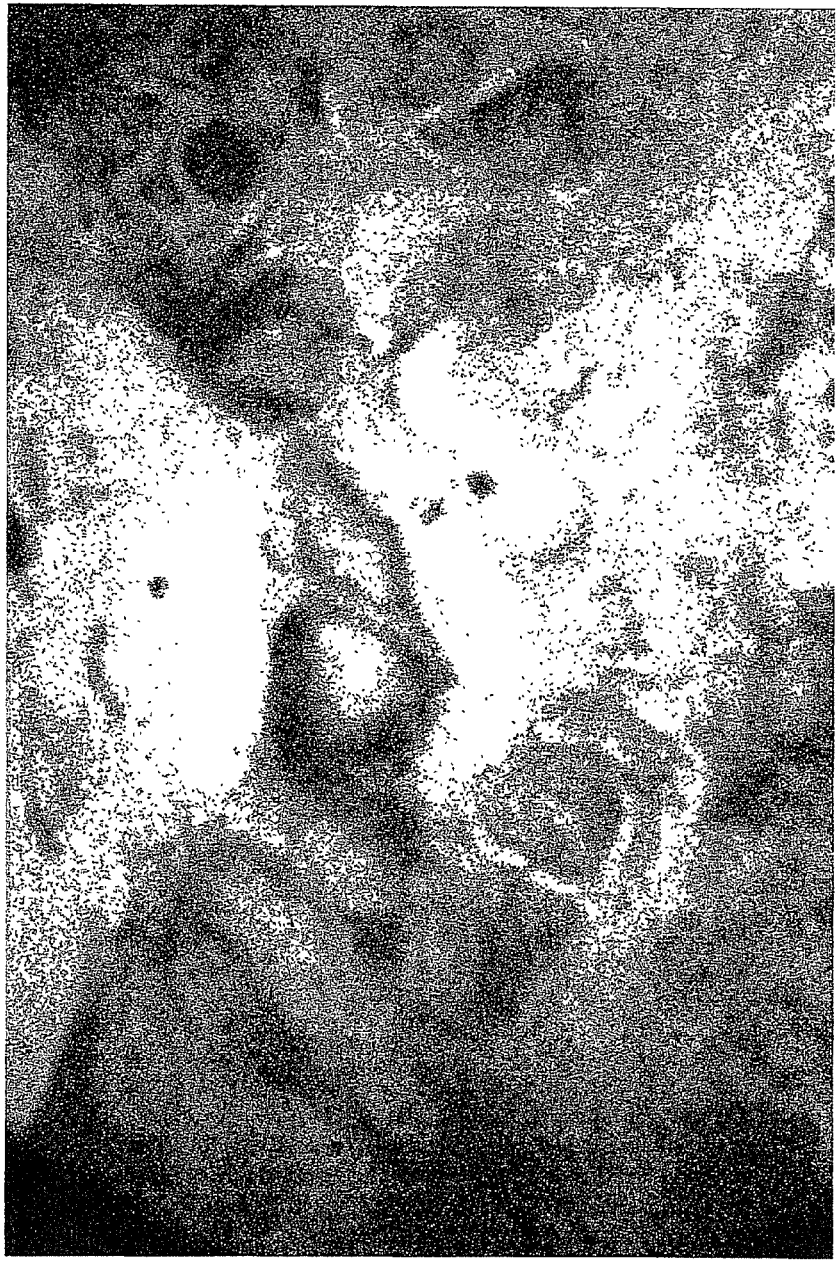
Figure 2C:
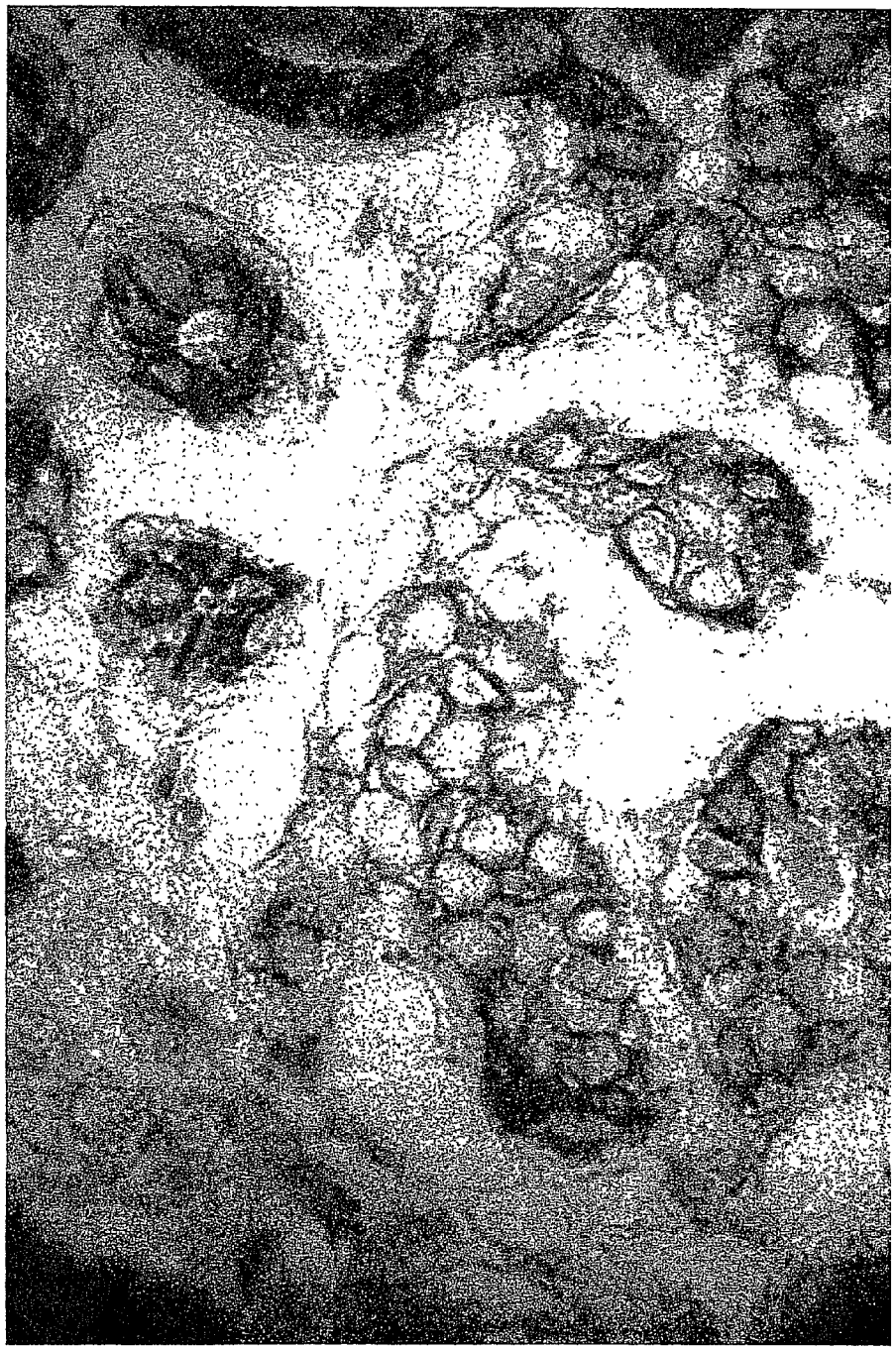
Figure 2D:
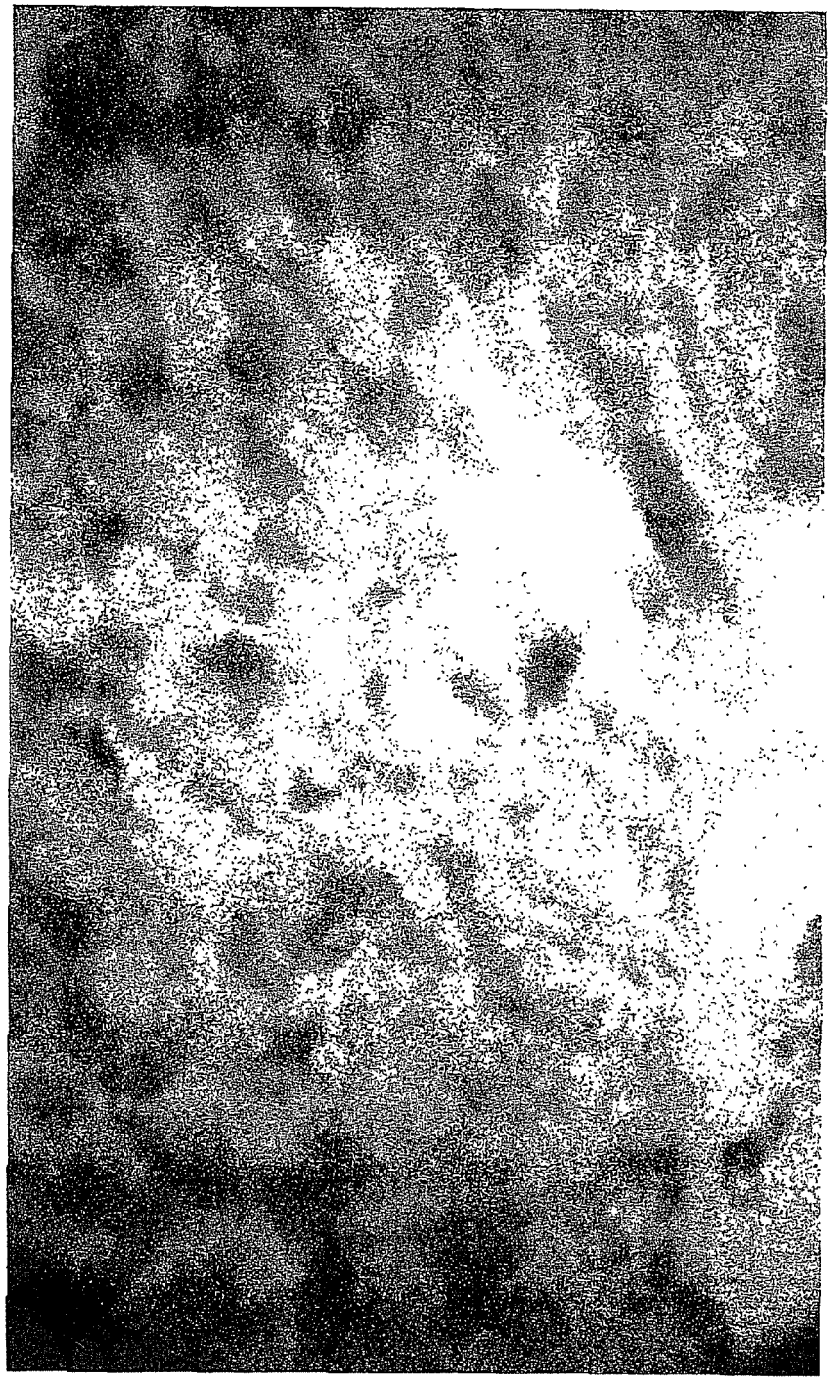
Figure 2E:
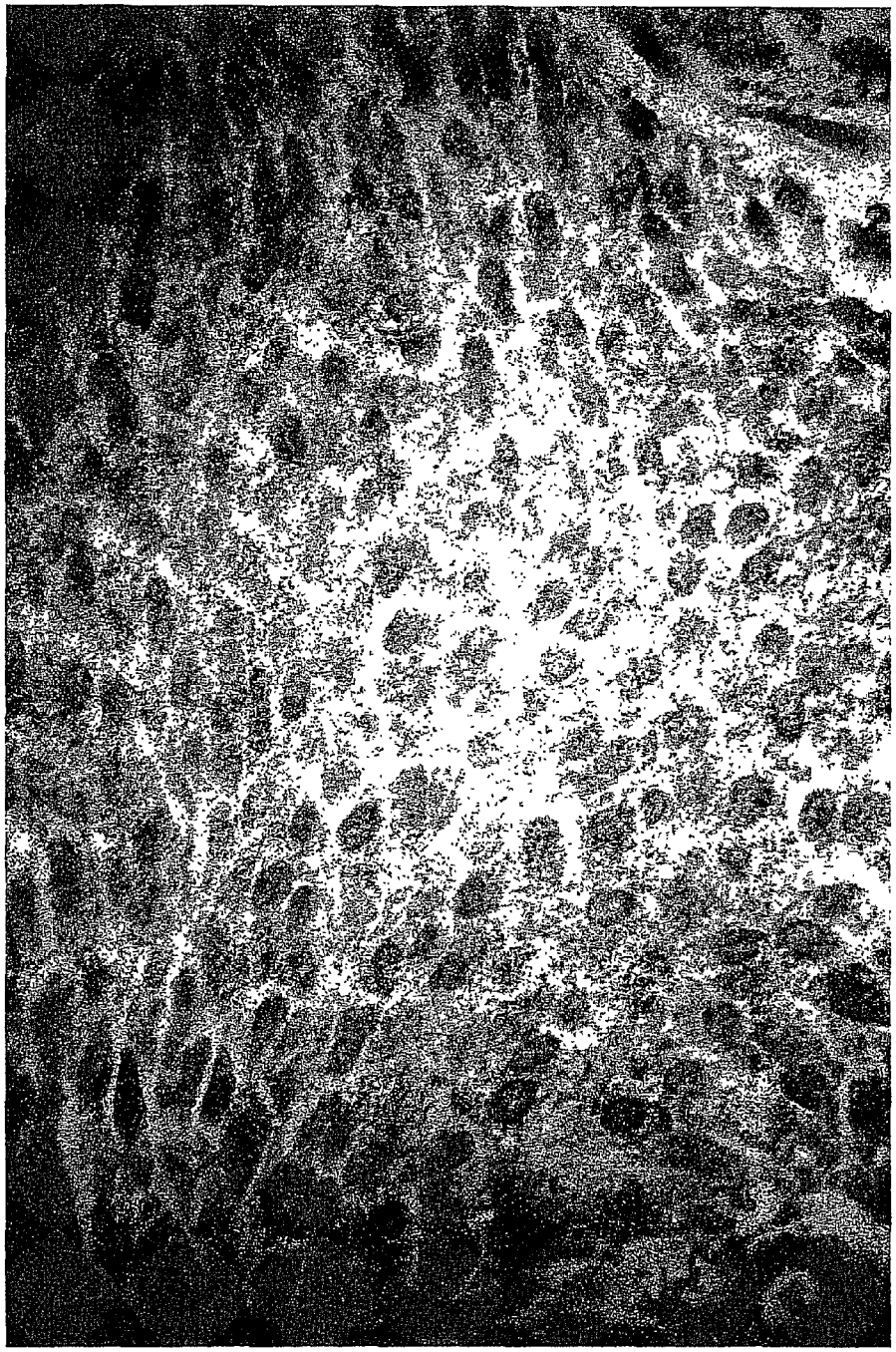

As a further example of tumor samples that were determined to be candidates for c-kit inhibitors, FIG. 2A-2E represent either bladder cancer samples (2A, 2D, and 2E) or breast cancer samples (2B and 2C) stained with antibodies to c-kit, SCF, and pAKT, as described above. FIG. 2B represents breast tumor sample 747 stained for c-kit. FIG. 2C represents breast tumor sample 848 stained for SCF. FIGS. 2D and 2E represent bladder tumor sample 920 stained for both c-kit (FIG. 2D) and for SCF (FIG. 2E), indicating that the patient is a good candidate for c-kit inhibitors. FIG. 2A represents the same bladder tumor sample 920 stained for pAKT.

Example 6

Image Analysis of c-Kit, SCF, and pAKT Protein Expression

Tumor samples were stained with antibodies to c-kit, SCF, and pAKT, and image analysis was used to determine the level of expression of these three proteins. The individual tumor samples analyzed included both samples of breast cancer (747, 848, 864, 895) and bladder cancer (920). The measurements were made using the CAS system as described in Bacus et al. (1997, *Anal. Quant. Cytol. Histol.* 19:316-28, incorporated herein by reference in its entirety).

Figure 3:
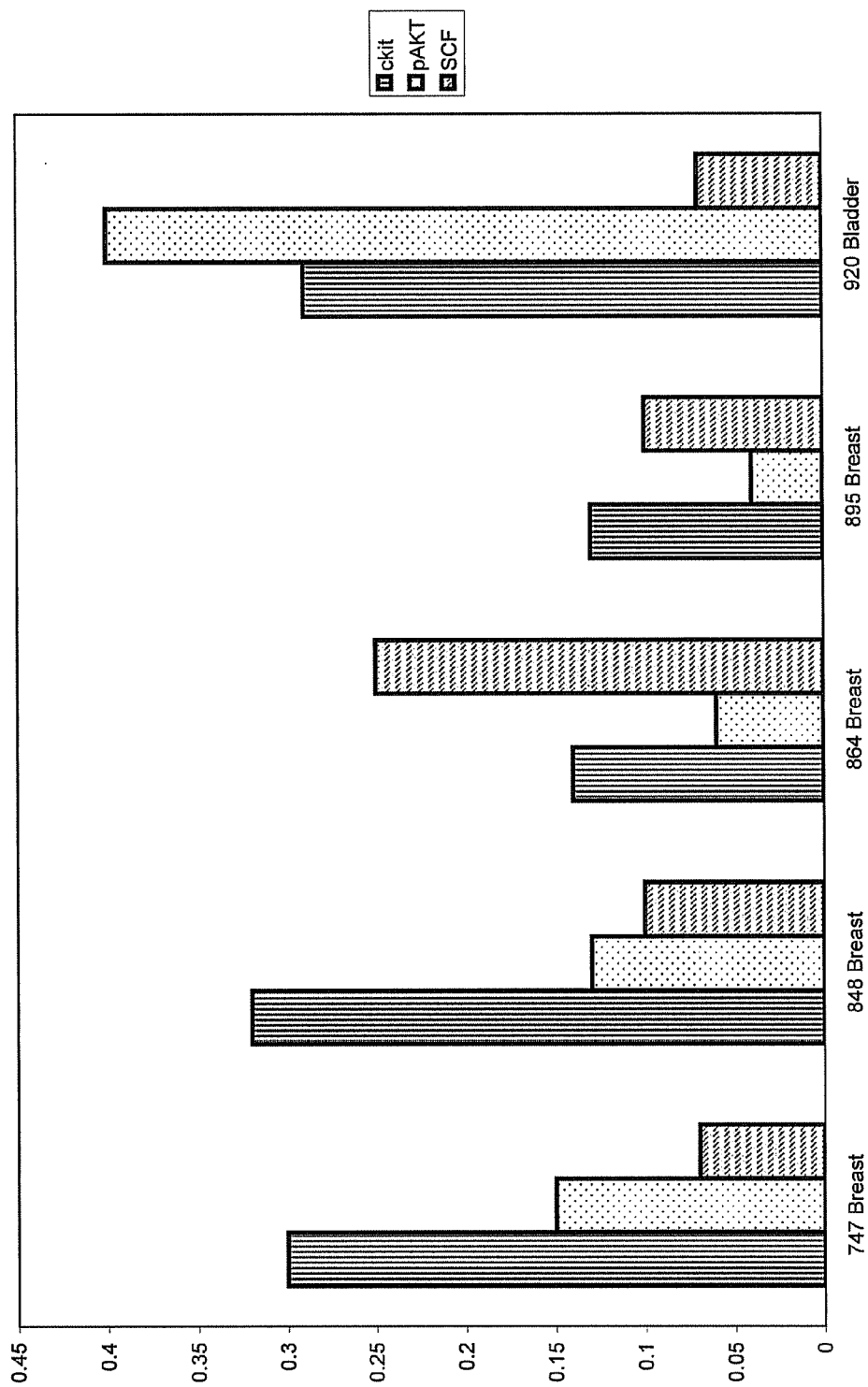
FIG. 3 is a bar graph showing the levels of c-kit, SCF, and pAKT measured by immunohistochemistry, combined with image analysis. The bar graph is expressed in units of optical density/pixel.

The levels of c-kit, SCF, and pAKT protein, expressed in units of optical density per pixel, are shown in Table II. FIG. 3 is a bar graph showing the levels of c-kit, SCF, and pAKT measured by image analysis and IHC staining in these five tumors showing that all three proteins were expressed, that all three proteins could be measured, and that there was considerable variation in the expression level of the three proteins. Presumably, these variations will affect drug susceptibility of the cancer.

TABLE II

| Image analysis quantification of c-kit, pAKT, and SCF in Tumor Sample, Expressed as Optical Density per Pixel | | | |
|---|---|---|---|
| Sample | c-kit | PAKT | SCF |
| "747" | 0.3 | 0.15 | 0.07 |
| "848" | 0.32 | 0.13 | 0.1 |
| "864" | 0.14 | 0.06 | 0.25 |
| "895" | 0.13 | 0.04 | 0.1 |
| "920" | 0.29 | 0.4 | 0.07 |

Example 7

Response to STI-571 in Breast Cancer Cell Lines

Figure 4:
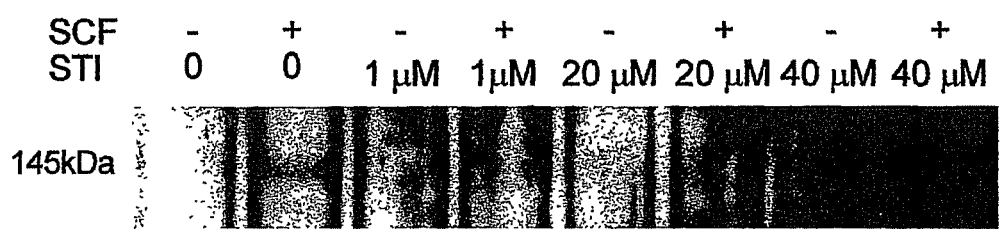
FIG. 4 is photograph of a western blot showing c-kit activation in breast cancer cells treated with SCF ligand in the presence of absence of STI-571 (Glivac, obtained from Novartis Pharmaceuticals). pc-kit was immunoprecipitated from MDA-MB-361 cell lysates (50 µg total protein), separated by gel electrophoresis and screened with anti-phosphotyrosine antibodies to detect active c-kit receptor. As expected, the c-kit receptor was activated by SCF treatment, but inhibited with as little as 1 µM STI-571.
Figure 5:
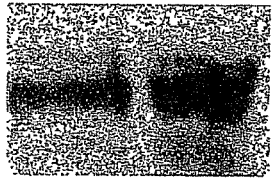
FIG. 5 is a photograph of a western blot of c-kit prepared from HeLa cells. Rabbit polyclonal antibodies against c-kit were obtained from NeoMarkers (1:200 dilution) and DAKO (1:400 dilution), and detected using HPR-conjugated antibodies against rabbit IgG (Amersham) and chemiluminescent substrate (NEN).
Figure 5:

The breast cancer cell line MDA-MB-361 was used to determine the response of a breast cancer line to a c-kit tyrosine kinase inhibitor, specifically Novartis agent STI-571 (GLIVEC™). FIG. 4 is a representation of a western blot showing c-kit activity in breast cancer cells treated with SCF ligand in the presence or absence of STI-571 in cell culture. The cell line was exposed to STI-571, varying from 1 µM to 40 µM, during a three-day cell culture. The cultured cell line and the control, untreated cell line were then lysed and cell lysates with 50 µg total protein were immunoprecipitated with both the Neomarkers CD117/c-Kit antibody clone Ab-6, and the DAKO CD117/c-Kit antibody clone A4502. FIG. 5 is a representation of a western blot of c-kit expression in HeLa cells probed with the same antibodies used to immunoprecipitate c-kit in the present experiment, clearly showing that both of the antibodies were capable of isolating c-Kit. FIG. 4, lane 1 shows that there is no activated c-kit expressed in the absence of its ligand, SCF. Lane 2 shows a distinct band at 145 kDa that indicates the isolation of activated c-kit when the cell culture is exposed to SCF. The remaining lanes (3-6) do not have a band at 145 kDa, demonstrating that there is no c-kit expression in the presence of as little as 1 µM STI-571. This result shows that STI-571 (GLIVEC™) is capable decreasing the amount of expression or activation of c-kit, in the presence of its ligand, SCF. Therefore, STI-571 (GLIVEC™) is identified as a compound that is useful to decrease expression or activation of c-kit, and correspondingly decrease activation of AKT.

It should be understood that the foregoing disclosure emphasizes certain specific embodiments of the invention and that all modifications or alternatives equivalent thereto are within the spirit and scope of the invention as set forth in the appended claims.

What I claim is:

1. A method comprising:
   immunohistochemically staining a first breast tissue or first breast cell sample from a breast cancer patient to whom a c-kit inhibitor has been administered with one or a plurality of detectably-labeled antibodies, wherein said one or plurality of detectably-labeled antibodies comprises at least one antibody that is immunologically specific for one or a plurality of biological markers selected from c-kit, SCF, pAKT, and pc-kit, wherein said detectable label is a chromogen or a fluorophore;

immunohistochemically staining a second breast tissue or second breast cell sample from the breast cancer patient with the one or the plurality of detectably-labeled antibodies, wherein the detectable label is a chromogen or a fluorophore, and wherein the second breast tissue or the second breast cell sample is taken from the breast cancer patient before the c-kit inhibitor has been administered; and determining an optical density of the chromogen or fluorophore in the first tissue or first cell sample and in the second tissue or second cell sample.

2. The method of claim 1, wherein the c-kit inhibitor is imatinib mesilate (Gleevec™).

3. The method of claim 1, wherein the one or the plurality of biological markers is c-kit.

4. The method of claim 1, wherein the c-kit inhibitor is imatinib mesilate (Gleevec™) and the one or the plurality of biological markers is c-kit.

5. A method of treating a patient having a breast cancer, said method comprising:

immunohistochemically staining a first breast tissue or first breast cell sample from a breast cancer patient to whom a c-kit inhibitor has been administered with one or a plurality of detectably-labeled antibodies, wherein said one or plurality of detectably-labeled antibodies comprises at least one antibody that is immunologically specific for one or a plurality of biological markers selected from c-kit, SCF, pAKT, and pc-kit, wherein said detectable label is a chromogen or a fluorophore;

immunohistochemically staining a second breast tissue or second breast cell sample from the breast cancer patient with the one or the plurality of detectably-labeled antibodies, wherein the detectable label is a chromogen or a fluorophore, and wherein the second breast tissue or the second breast cell sample is taken from the breast cancer patient before the c-kit inhibitor has been administered; and determining an optical density of the chromogen or fluorophore in the first tissue or first cell sample and in the second tissue or second cell sample; and treating the breast cancer patient with a c-kit inhibitor if decreased expression or activation of the one or the plurality of biological markers is determined.

6. The method of claim 5, wherein the c-kit inhibitor is imatinib mesilate (Gleevec™).

7. The method of claim 5, wherein the one or the plurality of biological markers is c-kit.

8. The method of claim 5, wherein the c-kit inhibitor is imatinib mesilate (Gleevec™) and the one or the plurality of biological markers is c-kit.

* * * * *